US010436702B2

(12) United States Patent
Anand et al.

(10) Patent No.: US 10,436,702 B2
(45) Date of Patent: Oct. 8, 2019

(54) CORROSION SENSOR, CORROSION MONITORING SYSTEM, AND METHOD OF QUANTIFYING CORROSION

(71) Applicant: GENERAL ELECTRIC COMPANY, Schenectady, NY (US)

(72) Inventors: Krishnamurthy Anand, Karnataka (IN); Paul Stephen Dimascio, Greer, SC (US); Sundar Amancherla, Dhahran (SA); Rebecca E. Hefner, Fountain Inn, SC (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 287 days.

(21) Appl. No.: 15/149,276

(22) Filed: May 9, 2016

(65) Prior Publication Data

US 2017/0322143 A1    Nov. 9, 2017

(51) Int. Cl.
*G01N 17/00* (2006.01)
*G01N 17/04* (2006.01)
*G01R 27/02* (2006.01)

(52) U.S. Cl.
CPC ........... *G01N 17/006* (2013.01); *G01N 17/04* (2013.01)

(58) Field of Classification Search
CPC .............................. G01N 17/006; G01N 17/04
See application file for complete search history.

(56) References Cited

U.S. PATENT DOCUMENTS

| 4,179,653 A | * | 12/1979 | Davies | G01N 17/00 324/700 |
| 4,882,537 A | | 11/1989 | Silverman | |
| 5,854,557 A | * | 12/1998 | Tiefnig | G01N 17/00 204/404 |
| 6,683,463 B2 | | 1/2004 | Yang et al. | |

(Continued)

FOREIGN PATENT DOCUMENTS

| EP | 2 375 235 A1 | 10/2011 |
| EP | 2 495 082 A1 | 9/2012 |
| GB | 2 150 300 A | 6/1985 |

OTHER PUBLICATIONS

Extended European Search Report and Opinion issued in connection with corresponding EP Application No. 17169613.1 dated Oct. 19, 2017.

*Primary Examiner* — Christopher P McAndrew
*Assistant Examiner* — Zannatul Ferdous
(74) *Attorney, Agent, or Firm* — McNees Wallace & Nurick LLC

(57) ABSTRACT

A corrosion monitoring system includes at least one corrosion sensor. The corrosion sensor includes a metallic plug having at least one opening, at least one ceramic sheath in the opening of the metallic plug, and a plurality of probes. Each probe has a central portion with a predetermined cross sectional area extending from the metallic plug. The ceramic sheath electrically isolates each first end and each second end of the probes from the metallic plug and the other first ends and second ends. The probes are sized to provide a distribution of predetermined cross sectional areas of the central portions. The corrosion monitoring system also includes a resistance meter measuring an ohmic resistance for at least one of the probes and a computer determining a corrosion rate by correlating a rate of change of the ohmic resistance to the corrosion rate of the probe.

19 Claims, 3 Drawing Sheets

(56) References Cited

U.S. PATENT DOCUMENTS

| | | |
|---|---|---|
| 7,180,309 B1 | 2/2007 | Yang |
| 7,309,414 B2 | 12/2007 | Yang |
| 7,678,260 B1 | 3/2010 | Yang et al. |
| 8,589,087 B2 * | 11/2013 | Martin .................. G01N 17/02 60/39.091 |
| 2005/0274628 A1 | 12/2005 | Yang |
| 2011/0273228 A1 * | 11/2011 | Kolias ....................... H01P 5/10 327/564 |
| 2012/0176148 A1 * | 7/2012 | Chey .................... G01N 17/046 324/700 |
| 2015/0128710 A1 * | 5/2015 | Vinogradov ......... G01N 29/223 73/627 |
| 2016/0091411 A1 * | 3/2016 | Hedtke ................. G01N 17/04 324/700 |

* cited by examiner

CORROSION SENSOR, CORROSION MONITORING SYSTEM, AND METHOD OF QUANTIFYING CORROSION

FIELD OF THE INVENTION

The present disclosure is directed to apparatus, systems, and methods for monitoring corrosion. More specifically the apparatus, systems, and methods of the present disclosure monitor corrosion experienced by turbine components measured as resistance changes across sensor probes.

BACKGROUND OF THE INVENTION

Modern high-efficiency combustion turbines have firing temperatures that exceed about 2000° F. (1093° C.), and firing temperatures continue to increase as demand for more efficient engines continues. Many components that form the combustor and "hot gas path" (HGP) turbine sections are directly exposed to aggressive hot combustion gases, for example, the combustor liner, the transition duct between the combustion and turbine sections, and the turbine stationary vanes and rotating blades and surrounding ring segments. In addition to thermal stresses, these and other components are also exposed to mechanical stresses and loads that further wear on the components.

Gas turbine engines may be operated using a number of different fuels. These fuels are combusted in the combustor section of the engine at temperatures at or in excess of 2000° F. (1093° C.), and the gases of combustion are used to rotate the turbine section of the engine, located aft of the combustor section of the engine. Power is generated by the rotating turbine section as energy is extracted from the hot gases of combustion. It is generally economically beneficial to operate the gas turbine engines using the most inexpensive fuel supply available. Two of the more abundant and inexpensive petroleum fuels are crude oil and heavy fuel oil. One of the reasons that they are economical fuels is that they are not heavily refined. Not being heavily refined, they may contain a number of impurities.

Heavy fuel oils typically contain several metallic elemental contaminants entrained as organic or inorganic complexes. These metallic elements, which may include one or more of sodium, potassium, vanadium, lead, and nickel, interact with oxygen and sulfur during combustion, including oxidation in the combustion plume, to form reaction products, including low melting point oxides. Sodium and potassium are conventionally removed prior to being injected into the combustion chambers by using an upstream fuel oil treatment system. Elements, such as vanadium and lead, however, are difficult to remove from the fuel by upstream accessories means.

Even the more refined liquid fuels used to power gas turbines are often residuals from distillation processes and typically contain significant levels of several contaminant elements. The oxides of these contaminants form low melting point compounds that flux the protective oxide scales and cause rapid corrosion during combustion.

The reaction products of these contaminants are problematic for at least two reasons. First, sodium vanadate, vanadium oxide, sodium sulfate, potassium sulfate, and lead oxide are extremely corrosive for the hot gas path alloys, including nickel-based and cobalt-based superalloys. Second, significant amounts of inhibitors may be needed to neutralize these corrosive oxides, such as, for example, inhibitors that form relatively inert vanadates from vanadium. But it is well known that in spite of the use of inhibitors, the components still undergo corrosion.

The molten oxides formed from the metal impurities react aggressively with native oxides formed in the nickel-based and cobalt-based alloys and induce rapid hot corrosion. Thermal barrier coatings on the nickel-based and cobalt-based alloys may be used to try to protect the parts and reduce corrosion, but some molten oxides, including vanadium oxide, are able to attack and react with some thermal barrier coatings to remove or degrade the thermal barrier coatings.

BRIEF DESCRIPTION OF THE INVENTION

In an exemplary embodiment, a corrosion sensor includes a metallic plug having at least one opening, at least one ceramic sheath in the opening of the metallic plug, and a plurality of probes. Each probe has a central portion with a predetermined cross sectional area extending from the metallic plug, a first end extending from the central portion into the ceramic sheath in the metallic plug, and a second end opposite the first end extending into the ceramic sheath in the metallic plug. The ceramic sheath electrically isolates each first end and each second end of the probes from the metallic plug and the other first ends and second ends. The probes are sized to provide a distribution of predetermined cross sectional areas of the central portions.

In another exemplary embodiment, a method of quantifying a corrosion rate of a turbine component includes measuring a plurality of ohmic resistances across a plurality of probes of a corrosion sensor during operation of a turbine comprising the turbine component. The corrosion sensor includes a metallic plug having at least one opening, at least one ceramic sheath in the opening of the metallic plug, and a plurality of probes. Each probe has a central portion with a predetermined cross sectional area extending from the metallic plug, a first end extending from the central portion into the ceramic sheath in the metallic plug, and a second end opposite the first end extending into the ceramic sheath in the metallic plug. The ceramic sheath electrically isolates each first end and each second end of the probes from the metallic plug and the other first ends and second ends. The probes are sized to provide a distribution of predetermined cross sectional areas of the central portions. The method also includes determining the corrosion rate by correlating a rate of change of the ohmic resistance of at least one of the probes to the corrosion rate of the probe.

In another exemplary embodiment, a corrosion monitoring system includes at least one corrosion sensor. The corrosion sensor includes a metallic plug having at least one opening, at least one ceramic sheath in the opening of the metallic plug, and a plurality of probes. Each probe has a central portion with a predetermined cross sectional area extending from the metallic plug, a first end extending from the central portion into the ceramic sheath in the metallic plug, and a second end opposite the first end extending into the ceramic sheath in the metallic plug. The ceramic sheath electrically isolates each first end and each second end of the probes from the metallic plug and the other first ends and second ends. The probes are sized to provide a distribution of predetermined cross sectional areas of the central portions. The corrosion monitoring system also includes a resistance meter measuring an ohmic resistance for at least one of the plurality of probes and a computer determining a corrosion rate by correlating a rate of change in the ohmic resistance to the corrosion rate of the probe.

Other features and advantages of the present invention will be apparent from the following more detailed description of the preferred embodiment, taken in conjunction with the accompanying drawings, which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided are exemplary systems and methods for measuring the corrosion experienced by turbine components. Embodiments of the present disclosure, in comparison to systems and methods not using one or more of the features described herein, provide a direct measurement of corrosion in a turbine system, produce corrosion data assessable by a field service technician, provide a real-time evaluation of corrosion, permit adjustment of inhibitor dosage without turbine shut down, or a combination thereof.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time-consuming, but would nevertheless be a routine undertaking of design, fabrication, and manufacture for those of ordinary skill having the benefit of this disclosure. Specific structural and functional details disclosed herein are not to be interpreted as limiting, but merely as a basis for the claims as a representative basis for teaching one skilled in the art to variously employ the present invention. Any modifications or variations in the depicted systems and methods, and such further applications of the principles of the invention as illustrated herein, as would normally occur to one skilled in the art, are considered to be within the spirit of this invention.

When introducing elements of various embodiments of the present invention, the articles "a", "an", "the", and "said" are intended to mean that there are one or more of the elements. The terms "comprising", "including", and "having" are intended to be inclusive and mean that there may be additional elements other than the listed elements.

Figure 1:
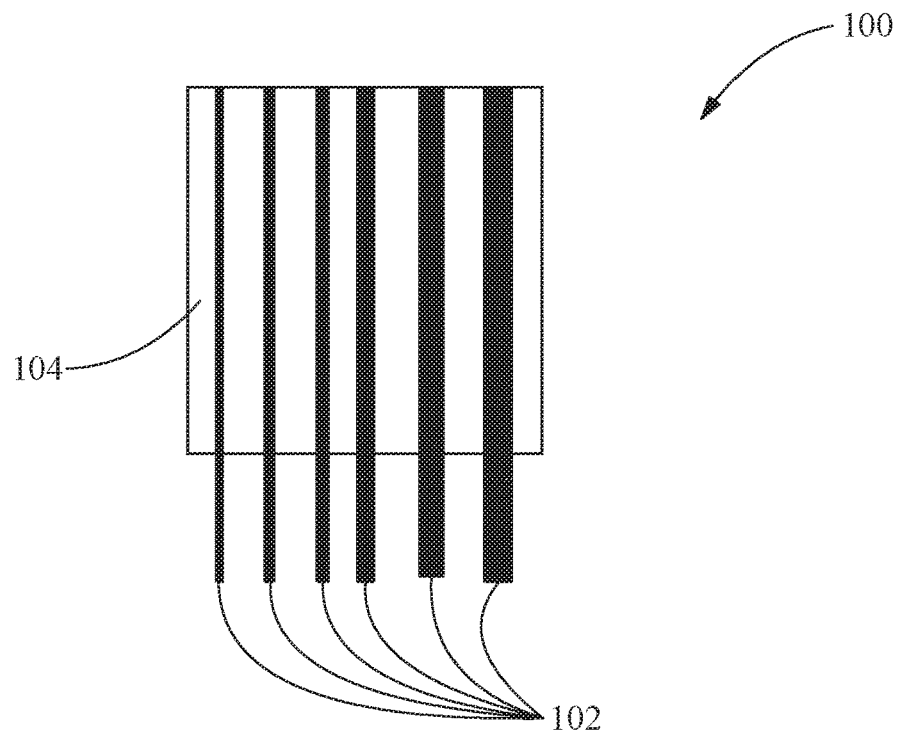
FIG. 1 is a schematic partial cross sectional side view of a corrosion sensor in an embodiment of the present disclosure.
Figure 2:
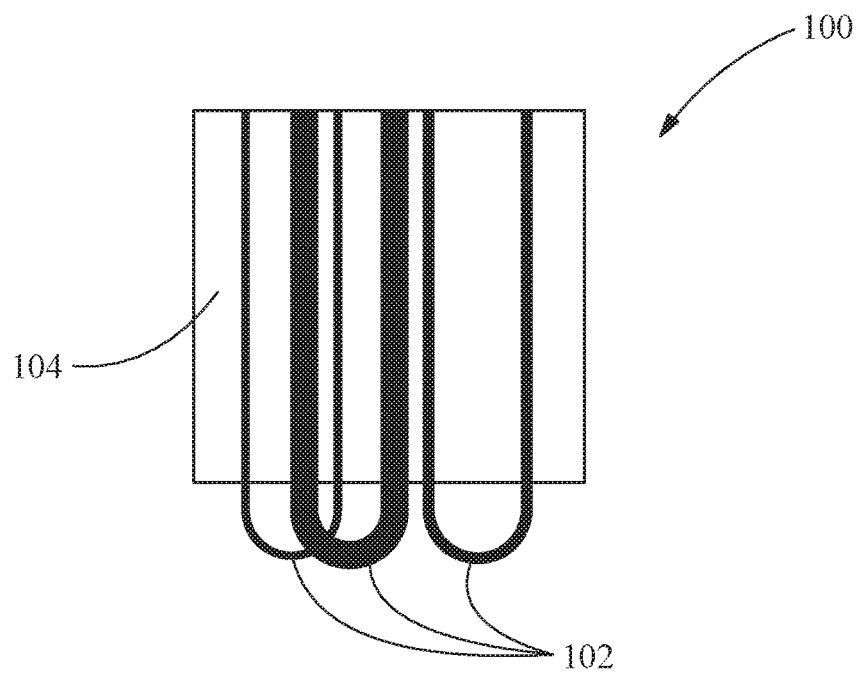
FIG. 2 is a schematic partial cross sectional front view of the corrosion sensor of FIG. 1.
Figure 3:
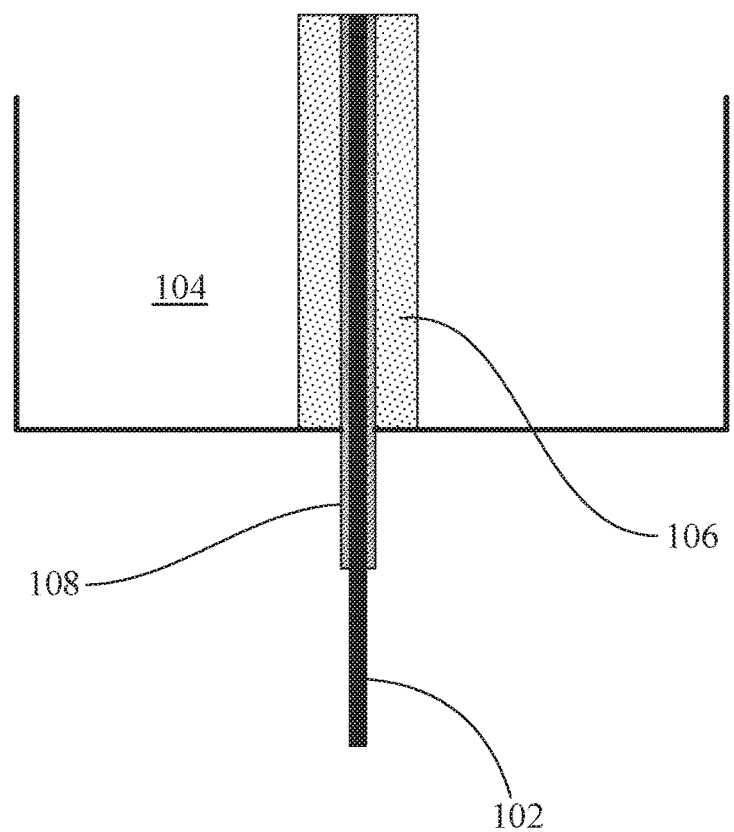
FIG. 3 is another schematic partial cross sectional view of the corrosion sensor of FIG. 1.

Referring to FIG. 1 through FIG. 3, a corrosion monitoring system includes at least one corrosion sensor 100, including a set of probes 102 and a metallic plug 104 receiving the probes 102. Although a set of six probes 102 is shown in FIG. 1, the set may include any number of probes greater than 1, including, but not limited to, two, at least two, three, at least three, four, at least four, five, at least five, six at least six, four to ten, or five to eight. Each probe 102 preferably has a substantially constant cross sectional area prior to use that is different from the cross sectional areas of the other probes 102. Each probe 102 is surrounded by a ceramic sheath 106 to prevent electrical contact between the probe 102 and the metallic plug 104. A ceramic pack 108 between the probe 102 and the ceramic sheath 106 and/or between the ceramic sheath 106 and the metallic plug 104 may fill any gaps while further promoting electrical isolation and holding the components of the corrosion sensor 100 together. As best seen in FIG. 2, the probes 102 are substantially U-shaped, more specifically in the shape of a capital "U", with the two ends extending into the metallic plug 104.

Figure 4:
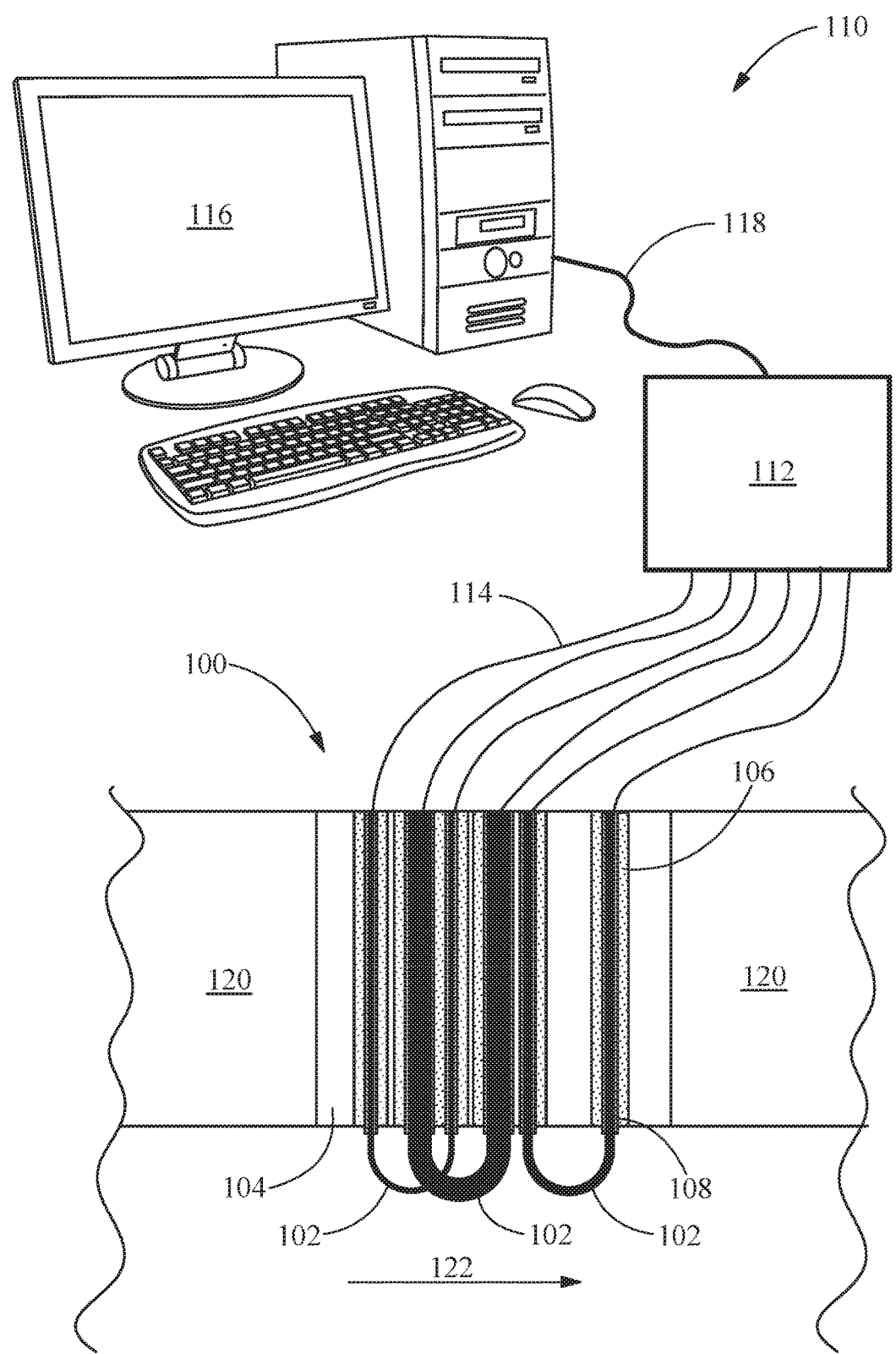
FIG. 4 is a schematic partial cross sectional view of a corrosion monitoring system including the corrosion sensor of FIG. 1.

FIG. 4 shows a corrosion monitoring system 110 including a corrosion sensor 100 installed in a turbine component 120 of a turbine. The corrosion monitoring system 110 also includes a resistance meter 112 in electrical communication with the probes 102 by way of wires 114. The corrosion monitoring system 110 further includes a computer 116 in communication with the resistance meter 112. The communication line 118 may be a wired line or a wireless line. The probes 102 extend from the metallic plug 104 and into the hot gas path (HGP) 122 of the turbine. The resistance meter 112 measures the electrical resistances of the probes 102 in situ in real time and determines a corrosion rate based on changes in the electrical resistances as a function of time during operation of the turbine.

Hot corrosion is determined based on resistance changes across the probes 102, with the set of probes 102 being able to measure losses for different discrete probe 102 diameters, for example, at 25 microns (1 mil), 50 microns (2 mil), 100 microns (4 mils), 250 microns (10 mils), and 500 microns (20 mils).

Although the probes 102 are shown as U-shaped, the probes 102 may have any contour that exposes a central portion to the HGP 122 while connecting the two ends to an electrical circuit. In some embodiments, the probes 102 may be contoured based on the clearance and geometry at the location where the corrosion sensor 100 is placed. In some embodiments, the central portion is a central curved portion. In some embodiments, the central portions of the probes 102 may be substantially straight and parallel to and in contact with the HGP 122 surface, instead of projecting into the HGP 122. For instance, each probe 102 may be a layer printed onto a ceramic sheath 106. The contour of the probe 102 does not affect the function as long as the cross sectional area is controlled. The resistance change with loss of cross sectional area due to corrosion is what creates the desired signal.

In some embodiments, the probes 102 are formed by machining, 3D metal printing, casting, bending a straight wire, or combinations thereof. The cross sectional area of the probe 102 may have any shape as long as the cross sectional area and shape are substantially unchanged in the central portion of the probe 102 prior to exposure to the HGP 122. In some embodiments, the cross sectional area of the probe 102 is a circle. In such embodiments, the cross sectional area may be described in terms of a radius or a diameter. In other embodiments, the cross sectional area may be oval, rectangular, or square.

The probes 102 may serve as a corrosion dashboard to dose inhibitors or pull-out hardware. The design of the corrosion sensor 100 is preferably modular such that the entire unit or individual probes 102 may be replaced during water washing or maintenance cycles. In other words, since the effective lifespan of the turbine or turbine component 120 may exceed the effective lifespan of the corrosion sensor 100, the spent corrosion sensor 100 is removable from the turbine component 120 and replaced with a new or working corrosion sensor 100. In some embodiments, the spent probes 102 are removable from the metallic plug 104 and replaced with new or replacement probes 102.

The corrosion sensor 100 includes a metallic plug 104 with at least one ceramic sheath 106 and a set of probes 102 having a central portion in the form of U-shaped metallic bends of differing cross sectional areas made out of the hot gas path alloy of interest. The metallic plug 104 includes holes for the insertion of the probes 102 having a central portion of different cross sectional areas. Each of these probes 102 is encapsulated in a ceramic sheath 106 to maintain electrical insulation from the metallic plug 104. A dense ceramic pack 108 seals the gaps between the ceramic sheath 106 and the probes 102 and seals the probe 102 to the metallic plug 104. Each of these bends of metal is insulated from the others by the ceramic sheaths 106 in the metallic plug 104.

The ohmic resistance of each of the bends of the probes 102 is measured continuously as a function of time. This increase is correlated to the cross sectional area loss of the probe 102, which in turn is correlated to the corrosion rate. The ohmic resistance may be measured by applying a predetermined voltage to each probe 102 and measuring the resulting current or by applying a predetermined current to each probe 102 and measuring the resulting voltage. The initial reading calibrates the system, taking into account the temperature component of the resistance. As the probes 102 thin due to corrosion, the resistance increases. The measured increase in resistance is calibrated to the cross sectional area loss of the probe 102, which in turn is converted to a corrosion rate.

A set of probes 102 with progressively greater cross sectional area provides a corrosion sensor 100 that continuously monitors corrosion rate of the HGP 122 hardware. The smallest cross sectional area probe 102 initially provides the most sensitive measure of corrosion. As the exposure of the corrosion sensor 100 to corrosion increases, the cross sectional area of each probe 102 decreases and the ohmic resistance increases. The measured increase in ohmic resistance is correlated to the cross sectional area loss of the probe 102, which in turn is correlated to the corrosion rate. When the cross sectional area of the smallest probe 102 becomes too small to provide a reliable resistance reading, the next smallest cross sectional area probe 102 has a decreased cross sectional area similar to the initial cross sectional area of the smallest cross sectional area probe 102 and therefore serves as the most sensitive probe 102 of the corrosion sensor 100 until it, too, has a cross sectional area too small to provide a reliable resistance reading. Thus, the set of probes 102 having progressively increasing cross sectional areas increases the useful life of the corrosion sensor 100. The probe 102 with the largest cross sectional area may serve as a corrosion odometer by reflecting the total amount of corrosion that has occurred since the corrosion sensor 100 was installed. Such a corrosion sensor 100 may be used both as a life odometer and as a feedback indicator to adjust the dosage of inhibitors being supplied in real time based on assessed corrosion rates.

The series of probes 102 with progressively higher cross sectional areas permits development of a corrosion sensor 100 that continuously monitors the corrosion rate of the HGP 122 hardware in real time. Such a device is very sensitive. A 250-micron diameter (0.049 mm$^2$) cross sectional area) probe 102, for example, shows a 50% increase in resistance for a 20% reduction in diameter, which corresponds to a loss of the outer 25 micron (1 mil) layer thickness of the probe 102 as corrosion loss. If the next probe 102 has a diameter of 500 microns (20 mils), a 50% increase in resistance corresponds to a 100-micron decrease in diameter. With six probes 102 starting from 250 microns (10 mils) in diameter to 4 mm (160 mils) in diameter, corrosion amounts may be monitored all the way from 25 microns (1 mil) to 500 microns (20 mils). For example, the diameters of the six probes 102 may be 250 microns (10 mils), 500 microns (20 mils), 1 mm (40 mils), 2 mm (80 mils), 3 mm (120 mils), and 4 mm (160 mils) such that the cross sectional areas of the probes 102 cover the range of about 0.05 mm$^2$ to about 13 mm$^2$. Alternatively, cross sectional areas may cover the range of about 0.01 mm$^2$ to about 100 mm$^2$, about 0.02 mm$^2$ to about 50 mm$^2$, about 0.04 mm$^2$ to about 25 mm$^2$, about 0.1 mm$^2$ to about 10 mm$^2$, or any range or sub-range therebetween.

The probes 102 having a central portion may be inserted through borescope plugs at the stage-1 and stage-3 locations of the turbine to monitor both type-1 and type-2 corrosion. Type-1 corrosion, as used herein, refers to hot corrosion that typically occurs in the temperature range of 850 to 950° C. (1560 to 1740° F.) starting with the condensation of fused alkali metal salts on the component surface. Type-2 corrosion, as used herein, refers to hot corrosion that typically occurs in the temperature range of 650 to 800° C. (1200 to 1470° F.) resulting from formation of low melting point mixtures (typically $Na_2SO_4$ and $CoSO_4/NiSO_4$).

Since the measured resistance change is caused by the cross sectional area change of the probe 102, the corrosion monitoring system 110 may measure a corrosion rate that is cumulative of multiple types of corrosion. The monitored corrosion rate is preferably not dependent on what mechanism or mechanisms are causing the corrosion to the probe 102.

The corrosion data may be interfaced through Mark VI or Mark VIe controllers (General Electric Company, Fairfield, Conn.) and independent control systems to adjust for inhibitor dosage and to make decisions on when to shut down the system for a more detailed inspection of the hardware.

In some embodiments, the corrosion sensors 100 are placed in at least two locations in the turbine to measure corrosion in different stages of the turbine. At least one corrosion sensor 100 may be placed aft of the stage-1 nozzle platform toward the casing side to measure corrosion events at close to the firing temperature. The sacrificial probes 102 may have the same base material and coating as what is used in the turbine. In some embodiments, three corrosion sensors 100 are placed along the circumference aft of the stage-1 nozzle platform.

Additionally, at least one corrosion sensor 100 may be placed close to the stage-3 or stage-4 nozzles, as appropriate, to capture the corrosion effects associated with both type-2 corrosion and with vanadium oxide being in the liquid state. Corrosion at this location is severe, if the inhibitor dosage is not right. In some embodiments, the dosage of the inhibitor is adjusted and the corrosion rate is monitored in real time in a feedback loop to optimize inhibitor dosage while minimizing the corrosion rate.

The resistivity measurements are preferably done from outside the casing and the outputs are hardwired to a dashboard that could be placed along with the Mark VI or Mark VIe control panel. In some embodiments, the corrosion sensor 100 from the hot section and the corrosion sensor 100 from the compressor inlet, if both deployed, are displayed together. A display panel, which is environment-related, captures corrosion events in the cold and hot sections of the turbine.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A corrosion sensor comprising:
   a metallic plug having at least one opening;
   at least one ceramic sheath in the opening of the metallic plug; and
   a plurality of probes, each of the plurality of probes having a central portion with a predetermined cross sectional area extending from the metallic plug, a first end extending from the central portion into the ceramic sheath in the metallic plug, and a second end opposite the first end extending into the ceramic sheath in the metallic plug;
   wherein the plurality of probes are formed of a material selected from the group consisting of a nickel-based superalloy and a cobalt-based superalloy;
   wherein the ceramic sheath electrically isolates the first end and the second end of each of the plurality of probes from the metallic plug and the other first ends and second ends;
   wherein the plurality of probes are sized to provide a distribution of predetermined cross sectional areas of the central portions; and
   wherein the predetermined cross sectional area of the central portion of a first probe of the plurality of probes is at least four times greater than the predetermined cross sectional area of the central portion of a second probe of the plurality of probes.

2. The corrosion sensor of claim 1 further comprising at least one ceramic pack filling a void space between one of the first ends and the ceramic sheath.

3. The corrosion sensor of claim 1, wherein the plurality of probes are U-shaped.

4. The corrosion sensor of claim 1, wherein the distribution of cross sectional areas covers the range of 0.05 mm$^2$ to 13 mm$^2$.

5. The corrosion sensor of claim 1, wherein the plurality of probes include at least five probes.

6. A method of quantifying a corrosion rate of a turbine component, comprising:
   measuring a plurality of ohmic resistances across a plurality of probes of a corrosion sensor in a hot gas path of a turbine comprising the turbine component during operation of the turbine, the corrosion sensor comprising: a metallic plug having at least one opening; at least one ceramic sheath in the opening of the metallic plug; and the plurality of probes, each of the plurality of probes having a central portion with a predetermined cross sectional area extending from the metallic plug, a first end extending from the central portion into the ceramic sheath in the metallic plug, and a second end opposite the first end extending into the ceramic sheath in the metallic plug, the ceramic sheath electrically isolating the first end and the second end of each of the plurality of probes from the metallic plug and the other first ends and second ends, the plurality of probes being sized to provide a distribution of predetermined cross sectional areas of the central portions, and the predetermined cross sectional area of the central portion of a first probe of the plurality of probes being at least four times greater than the predetermined cross sectional area of the central portion of a second probe of the plurality of probes;
   wherein the plurality of probes are formed of a material selected from the group consisting of a nickel-based superalloy and a cobalt-based superalloy; and
   determining the corrosion rate by correlating a rate of change in the ohmic resistance of at least one of the plurality of probes to the corrosion rate of the at least one of the plurality of probes.

7. The method of claim 6 further comprising locating the plurality of probes in a hot gas path of the turbine.

8. The method of claim 6 further comprising locating the corrosion sensor aft of a stage-1 nozzle platform of the turbine.

9. The method of claim 6 further comprising locating the corrosion sensor in a third stage or a fourth stage of the turbine.

10. The method of claim 6 further comprising adjusting a dosage of inhibitor supplied to the turbine based on the corrosion rate.

11. The method of claim 6, wherein the measuring and the determining occur in real time during operation of the turbine.

12. The method of claim 6, wherein the plurality of probes are U-shaped.

13. The method of claim 6, wherein the distribution of cross sectional areas covers the range of 0.05 mm$^2$ to 13 mm$^2$.

14. A corrosion monitoring system comprising:
   at least one corrosion sensor comprising:
      a metallic plug having at least one opening;
      at least one ceramic sheath in the opening of the metallic plug; and
      a plurality of probes, each of the plurality of probes having a central portion with a predetermined cross sectional area extending from the metallic plug, a first end extending from the central portion into the ceramic sheath in the metallic plug, and a second end opposite the first end extending into the ceramic sheath in the metallic plug, the ceramic sheath electrically isolating each first end and each second end of the plurality of probes from the metallic plug and the other first ends and second ends, the plurality of probes being formed of a material selected from the group consisting of a nickel-based superalloy and a cobalt-based superalloy, the plurality of probes being sized to provide a distribution of predetermined cross sectional areas of the central portions, and the predetermined cross sectional area of the central portion of a first probe of the plurality of probes being at least four times greater than the predetermined cross sectional area of the central portion of a second probe of the plurality of probes;
   a resistance meter measuring an ohmic resistance for at least one of the plurality of probes; and a computer determining a corrosion rate by correlating a rate of change of the ohmic resistance to the corrosion rate of the at least one of the plurality of probes.

15. The corrosion monitoring system of claim 14 further comprising a display panel displaying the corrosion rate determined by the computer.

16. The corrosion monitoring system of claim 14, wherein the plurality of probes are U-shaped.

17. The corrosion monitoring system of claim 14, wherein the distribution of cross sectional areas covers the range of 0.05 mm² to 13 mm².

18. The corrosion sensor of claim 1, wherein the predetermined cross sectional area of the central portion of the first probe of the plurality of probes is at least sixteen times greater than the predetermined cross sectional area of the central portion of the second probe of the plurality of probes.

19. The corrosion sensor of claim 1, wherein the predetermined cross sectional area of the central portion of the first probe of the plurality of probes is at least 100 times greater than the predetermined cross sectional area of the central portion of the second probe of the plurality of probes.

* * * * *